(12) United States Patent  
Suzuki

(10) Patent No.: US 7,288,103 B2
(45) Date of Patent: Oct. 30, 2007

(54) LINK DEVICE FOR SURGICAL TOOL AND SURGICAL TOOL

(75) Inventor: Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 528 days.

(21) Appl. No.: 10/862,760

(22) Filed: Jun. 7, 2004

(65) Prior Publication Data

US 2004/0249411 A1 Dec. 9, 2004

(30) Foreign Application Priority Data

Jun. 9, 2003 (JP) ............................. 2003-163570

(51) Int. Cl.
*A61B 17/28* (2006.01)
*A61B 17/42* (2006.01)
*A61B 17/44* (2006.01)

(52) U.S. Cl. ...................... 606/205; 606/206; 606/207; 606/210

(58) Field of Classification Search ................ 606/205, 606/206, 207
See application file for complete search history.

(56) References Cited

U.S. PATENT DOCUMENTS 5,383,888 A * 1/1995 Zvenyatsky et al. ........ 606/206

5,766,205 A 6/1998 Zvenyatsky et al.

FOREIGN PATENT DOCUMENTS

| EP | 1 101 446 A2 | 5/2001 |
|---|---|---|
| EP | 1 250 891 A2 | 10/2002 |
| JP | 2001-299768 | 10/2001 |

\* cited by examiner

*Primary Examiner*—Michael J. Hayes
*Assistant Examiner*—Michael G. Mendoza
(74) *Attorney, Agent, or Firm*—Scully, Scott, Murphy & Presser, P.C.

(57) ABSTRACT

In a link device for surgical tool and a surgical tool suitable for used with an endoscope, the diameter of an insertion section can be made narrow. A multi-free forceps (surgical tool) is used as a soft surgical tool for use with an endoscope. The multi-free forceps comprises a link device for surgical tool that is inserted into a human cavity. The link device for surgical tool comprises a pipe-like insertion section, a surgical section that connects to a tip of the insertion section, and a control section that controls the surgical section. A base side of a deviating link member is securely connected to a first control axis member, and a base side of the deviating link member that forms the surgical section side extends in parallel to the first control axis member at a position that is further to the inside than the outer peripheral face of the insertion section, while deviating further to the outside of the diameter direction than the central axis of the first control axis member.

3 Claims, 9 Drawing Sheets

CROSS SECTION ALONG X-X

CROSS SECTION ALONG Y-Y

CROSS SECTION ALONG Z-Z

LINK DEVICE FOR SURGICAL TOOL AND SURGICAL TOOL

BACKGROUND OF THE INVENTION

1. Field of the Invention

This invention relates to a link device for surgical tool that connects to a forceps member and the like, and a surgical tool.

This application is based on Japanese Patent Application No. 2003-163570, the contents of which are incorporated herein by reference.

2. Description of the Related Art

In surgical treatment performed by inserting a surgical instrument into human abdominal cavities, the abdominal cavities are minimized so as to reduce the burden on the patient; consequently, the treatment must be performed by inserting the surgical instruments of limited numbers and sizes into cavities. To accomplish this, after inserting the surgical instrument into an abdominal cavity, the surgeon uses a forceps for endoscope, which enables him to perform multi-free operations via a one-directional operation (e.g. see Japanese Patent Application, First Publication No. 2001-299768 (FIG. 3)).

According to the multi-free forceps of Japanese Patent Application, First Publication No. 2001-299768 (FIG. 3), connecting pins and supporting pivots for supporting a connecting member are arranged around the central axis of drive rods, which deviate from their central axis in order to avoid the connecting pins and the supporting pivots. This makes it possible to perform an oscillating operation by assembling a link device, which is connected to control axis members comprising a plurality of operating rods, it being possible to the direction of the device section by a rotating the handle while the multi-free forceps is inserted so as to clasp the organism, and stitch up the organism and the like.

SUMMARY OF THE INVENTION

A link device for surgical tool of this invention comprises a pipe-like insertion section having a control axis member extending in one direction therein, the control axis member being capable of moving forward and backward; a surgical section, which is connected via the control axis member and at least one link member, the surgical section being controlled by the forward and backward movement of the control axis member. When using one of the link members that is directly connected to a tip of the control axis member as a deviating link member, a tip of the deviating link member is connected to the surgical section directly or via another link member. The deviating link member is formed extending in parallel with the control axis member at a position deviated to the outside from the central axis of the control axis member.

A surgical tool of this invention comprises the link device for surgical tool described above, wherein the surgical section is a surgical tool capable of performing an oscillating operation; the center of rotation of the oscillating operation is deemed a first rotational axis, and the tip side of the deviating link member is arranged further to the outside of the diameter direction of the insertion section than the first rotational axis.

In the surgical tool of this invention, the surgical section comprises a first forceps member and a second forceps member, which are rotatably connected to a second rotational axis at a base side; the second rotational axis being arranged further to the tip side of the first forceps member than the first rotational axis; the insertion section using the control axis member as a first control axis member, and having a second control axis member in line therewith, the second control axis member being capable of moving forward and backward inside the insertion section; the deviating link member being connected to a base of the first forceps member directly or via the link member, the first forceps member being capable of being rotated around the second rotational axis by the forward and backward movement of the first control axis member; the second control axis member being connected to the base of the second forceps member directly or via the link member, and the second forceps member being capable of being rotated around the first rotational axis by the forward and backward movement of the second control axis member.

DESCRIPTION OF THE PREFERRED EMBODIMENTS

Figure 1:
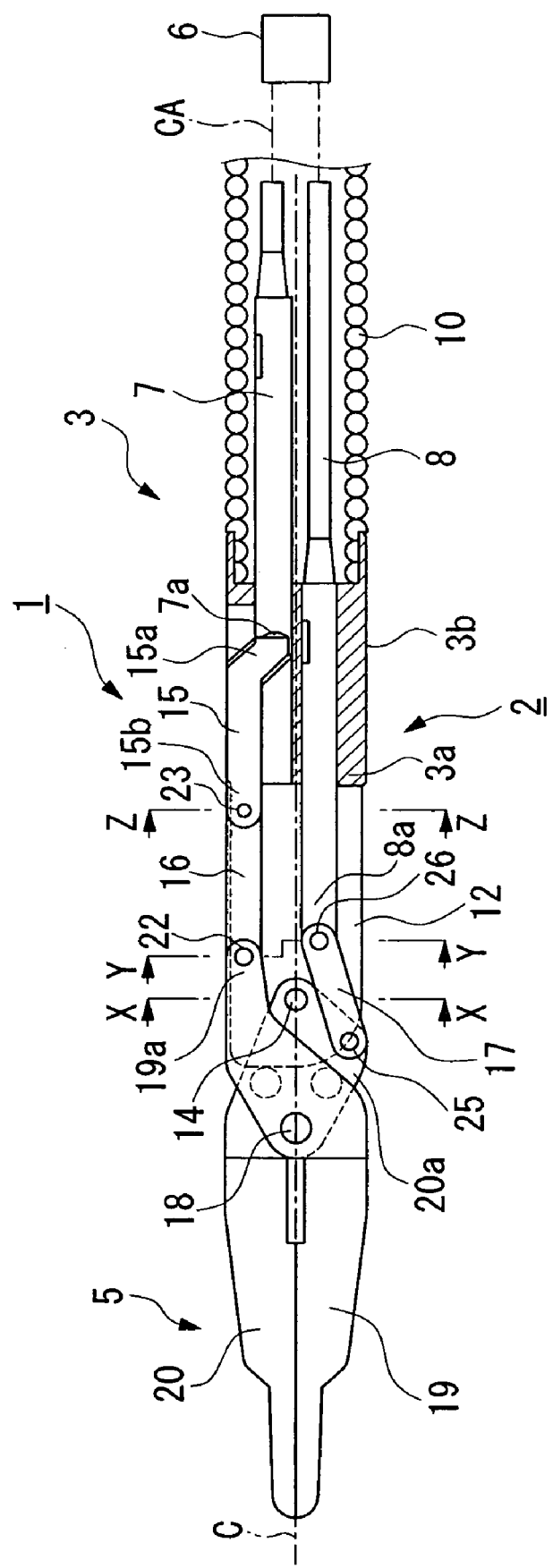
FIG. 1 is a cross-sectional arrow diagram taken along a central axis showing primary parts of a multi-free forceps according to an embodiment of this invention.

A preferred embodiment of the invention will be explained with reference to FIGS. 1 to 3.

The multi-free forceps (surgical tool) 1 according to this invention is used as a flexible surgical tool that is used with an endoscope. As shown in FIG. 1, the multi-free forceps 1 has a link device for surgical tool 2, which is inserted into a bodily cavity. The link device for surgical tool 2 comprises an insertion section 3 that extends in a pipe-like shape, a surgical section 5 that connects to a tip of the insertion section 3, and a control section 6 that controls the surgical section.

The insertion section 3 comprises a first control axis member 7 and a second control axis member 8, which extend in parallel in the same direction, and a pipe-like seize member 10 that covers their outer sides. A tip 3a of the insertion section 3 is formed in a fork-like shape, and, as shown in FIGS. 1 and 2, a pair of cover members 12 and 13 are provided on both sides of a slit 11, running along a flat face P that comprises the first control axis member 7 and the second control axis member 8.

A first pivotal supporting member (first rotational axis) 14 runs through the pair of cover members 12 and 13 from vertically above the flat face P, and forms the rotational center of the surgical section 5 while it is oscillating.

Figure 2A:
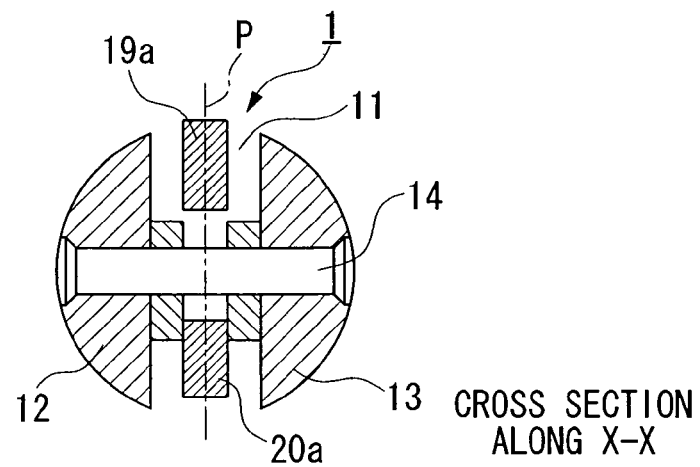
FIGS. 2A, 2B, and 2C are arrow diagrams respectively showing cross-sectional views along the faces X-X, Y-Y, and Z-Z of FIG. 1.

As shown in FIG. 1, a tip 7a of the first control axis member 7 connects to a base 15a of a deviating link member 15, which transmits the force of the control section 6, a tip 15b of the deviating link member 15 being connected to a first link member 16, which further transmits the transmitted force to the surgical section 5. A tip 8a of the second control axis member 8 connects to a second link member 17, which further transmits the force that was transmitted in the second control axis member 8 to the surgical section 5.

The link members can be driven within the flat face P that comprises the first control axis member 7 and the second control axis member 8.

The tip 15b side of the deviating link member 15 is nearer the inside than the outer peripheral face 3b of the insertion section 3, and extends in parallel with the first control axis member 7 at a position that is deviated further to the outside of the diameter direction than the central axis CA of the first control axis member 7. That is, the tip 15b of the deviating link member 15 is provided further to the outside of the diameter direction of the insertion section 3 than the first pivotal supporting member 14.

Figure 2B:
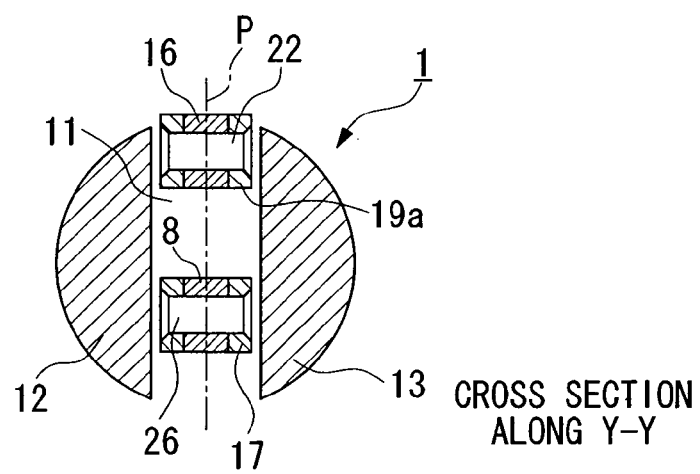
Figure 2C:
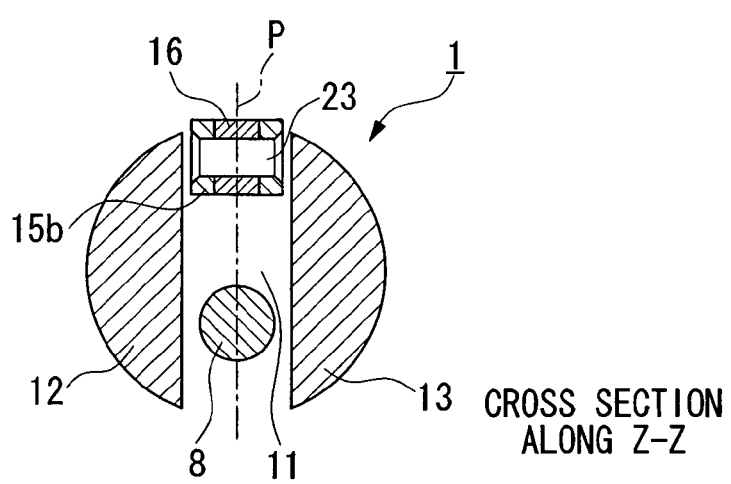

As shown in FIG. 2C, the tip 15b of the deviating link member 15 is arranged in the slit 11 in the tip 3a of the insertion section 3.

The surgical section 5 can be oscillated around the first pivotal supporting member 14, and comprises a first forceps member 19, which is rotatably connected via a second pivotal supporting member (second rotational axis) 18, and a second forceps member 20.

The base 19a of the first forceps member 19 connects to a first link member 16, and the base 20a of the second forceps member 20 connects to a second link member 17.

The second pivotal supporting member 18 is provided further to the tip side of the first forceps member 19 than the first pivotal supporting member 14.

As shown in FIG. 2B, the first forceps member 19 is rotatably connected to the first link member 16 via a third pivotal supporting member 22, and, as shown in FIG. 2C, the deviating link member 15 is rotatably connected to the first link member 16 via a fourth pivotal supporting member 23.

The second forceps member 20 is rotatably connected to the second link member 17 via a fifth pivotal supporting member 25, and, as shown in FIG. 2B, the second link member 17 is rotatably connected to the second control axis member 8 via a sixth pivotal supporting member 26.

Subsequently, a control method of the multi-free forceps 1 of this embodiment will be explained.

Let us assume that the first forceps member 19 and the second forceps member 20 are closed along a central axis C, as shown in FIG. 1.

From this state, the first control axis member 7 is moved forward to the surgical section 5 side by manipulating the control section 6. Since the deviating link member 15 also moves forward in the same direction as the first control axis member 7, a forward-moving force is transmitted to the fourth pivotal supporting member 23. The first link member 16 extends in a different direction from the direction in which the second pivotal supporting member 18 joins the third pivotal supporting member 22 on the first forceps member 19, and consequently, the force is transmitted as rotational movement to the first link member 16. Therefore, the fourth pivotal supporting member 23 moves forward while the first link member 16 rotates around the fourth pivotal supporting member 23. In addition, the third pivotal supporting member 22 moves away from the central axis C, and the first forceps member 19 moves away from the second forceps member 20 with the second pivotal supporting member 18 as its base point.

Figure 3:
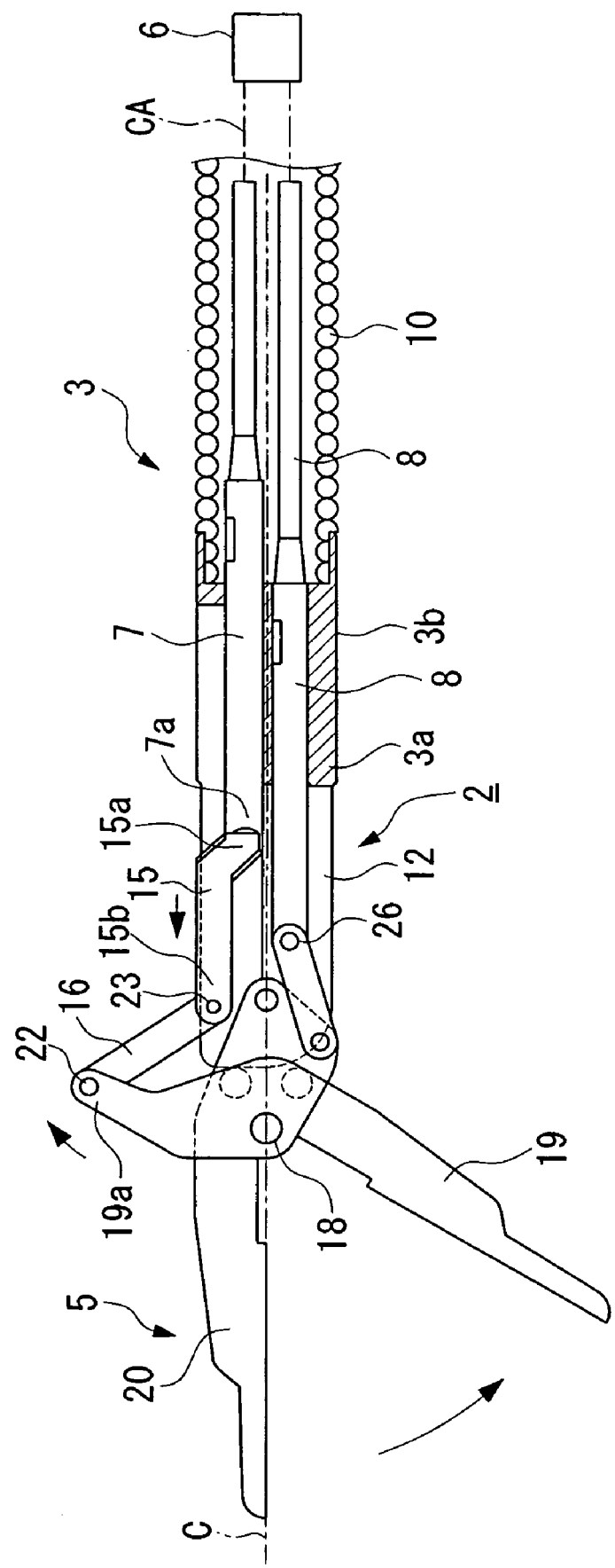
FIG. 3 is a side view of primary parts of the multi-free forceps according to the embodiment of this invention in an open state, with one portion thereof cut away.

By this operation, the first forceps member 19 and the second forceps member 20 can be opened, with the second pivotal supporting member 18 as the base point, to the state shown in FIG. 3.

At this time, since the tip 15b of the deviating link member 15 is further to the inside than the outer peripheral face 3b of the insertion section 3 and extends in parallel with the first control axis member 7 at a position deviated further to the outside of the central axis C than the first control axis member 7, the tip 15b of the deviating link member 15 moves to the surgical section 5 side without interfering with the first pivotal supporting member 14.

To close the second forceps member 20 so that it is once again opposite the first forceps member 19, the first control axis member 7 is moved backward to the control section 6 side by manipulating the control section 6.

At this time, the backward force becomes rotational movement to the first link member 16, rotating the first link member 16 in the opposite direction to that mentioned above, so that the third pivotal supporting member 22 moves nearer to the central axis C. As a result of this movement, the tip side of the first forceps member 19 rotates toward the second forceps member 20 with the second pivotal supporting member 18 as its base point, closing the first forceps member 19 and the second forceps member 20.

Figure 4:
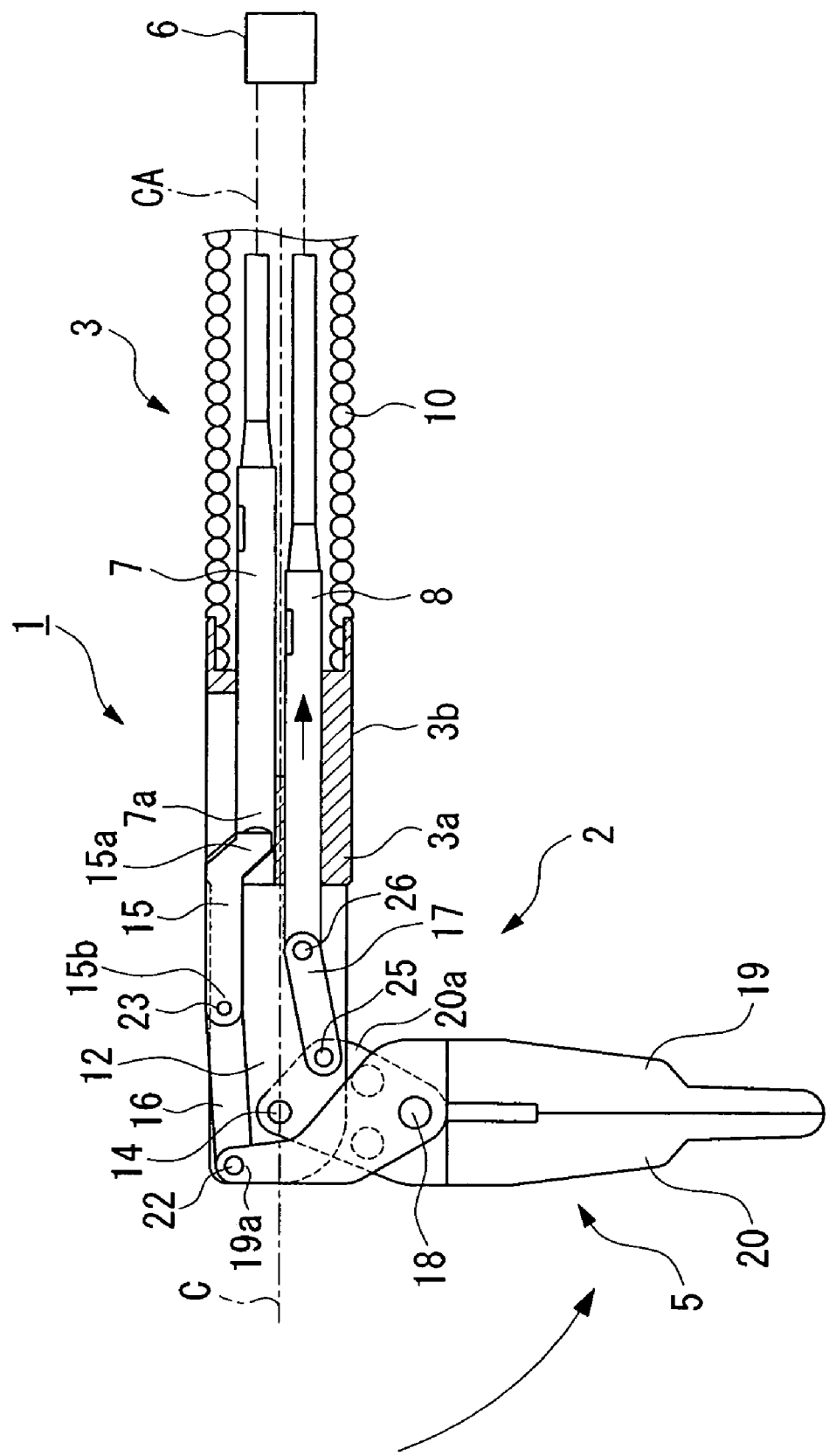
FIG. 4 is a side view of primary parts of the multi-free forceps according to the embodiment of this invention in an oscillated state, with one portion thereof cut away.

Subsequently, as shown in FIG. 4, an oscillating operation of rotating the second pivotal supporting member 18 around the first pivotal supporting member 14 will be explained.

It is assumed here that the first forceps member 19 and the second forceps member 20 are closed along the central axis C, as shown in FIG. 1.

In this state, the second control axis member 8 is moved backward toward the control section 6 side by manipulating the control section 6, whereby the second link member 17 moves backward. Consequently, the fifth pivotal supporting member 25 rotates around the first pivotal supporting member 14, moving nearer to the insertion section 3 side than the first pivotal supporting member 14.

In this way, the oscillating operation is performed by rotating the second forceps member 20 with the first forceps member 19 around the first pivotal supporting member 14, and moving them toward the second link member 17.

To oscillate the first forceps member 19 and the second forceps member 20 so that they are positioned once again along the central axis C, the second control axis member 8 is moved forward in the tip direction by manipulating the control section 6.

The forward force at this time moves the second link member 17 forward, and rotates the fifth pivotal supporting member 25 around the first pivotal supporting member 14 in the opposite direction to that mentioned above. As a consequence, the tip side of the second forceps member 20 rotates with the first forceps member 19, and thereby oscillates.

Figure 5:
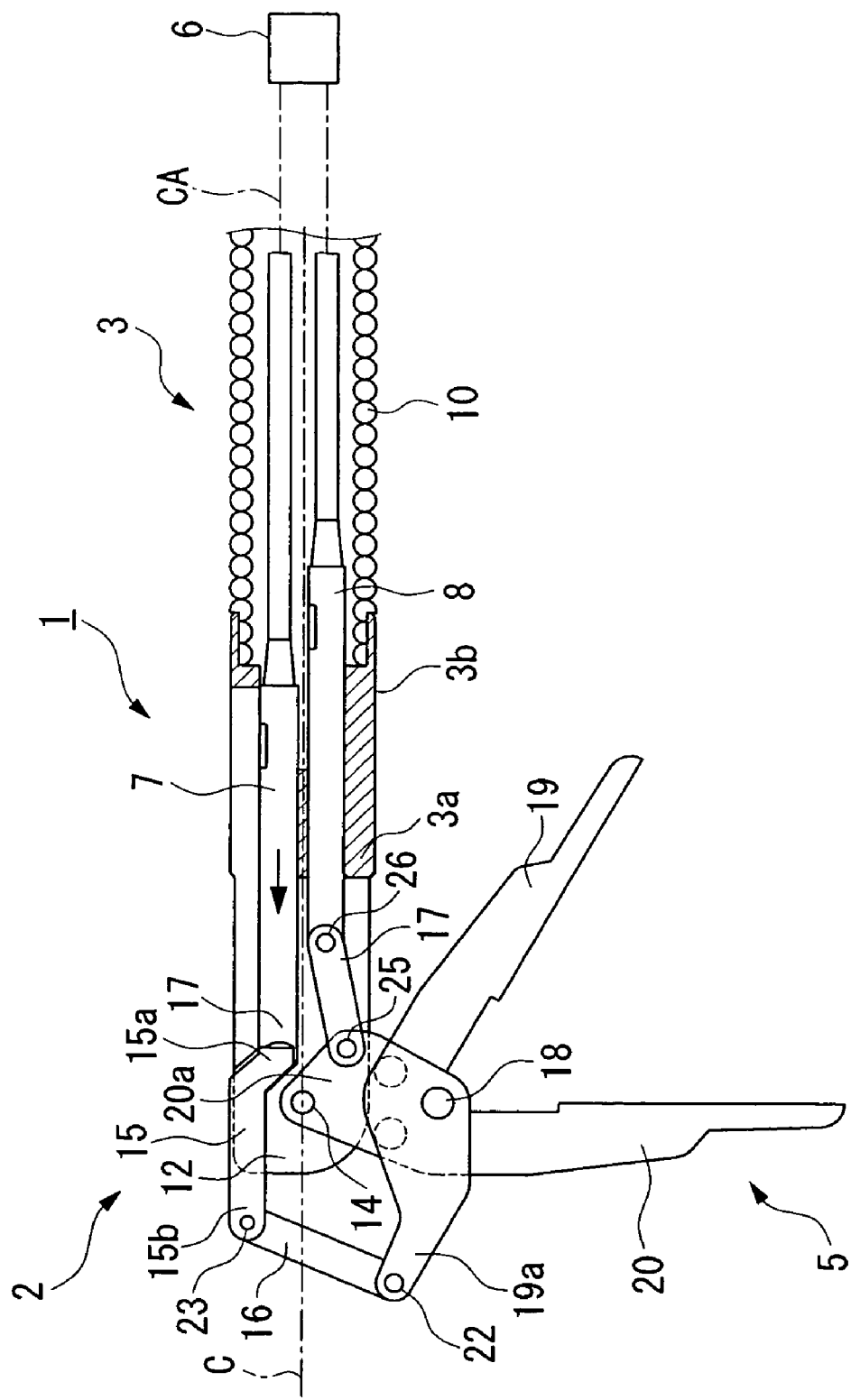
FIG. 5 is a side view of opened primary parts of the multi-free forceps according to the embodiment of this invention in an oscillated state, with one portion thereof cut away.
Figure 6:
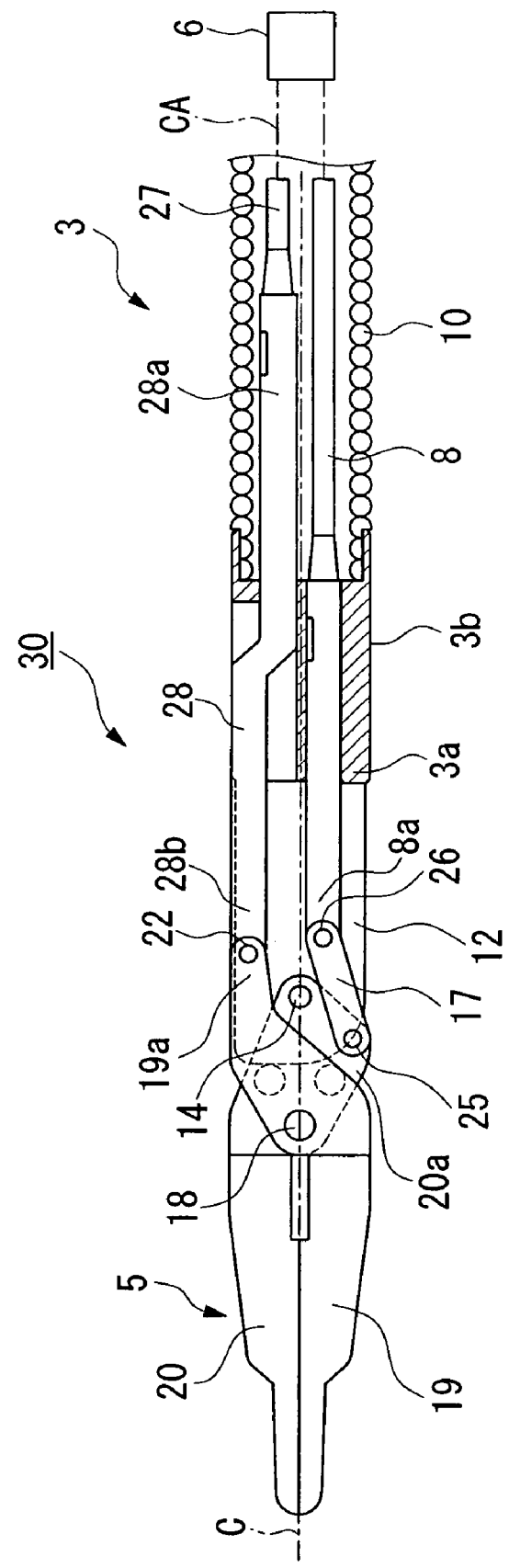
FIG. 6 is a cross-sectional arrow diagram of a central axis showing primary parts of another embodiment of the multi-free forceps according to this invention.
Figure 7:
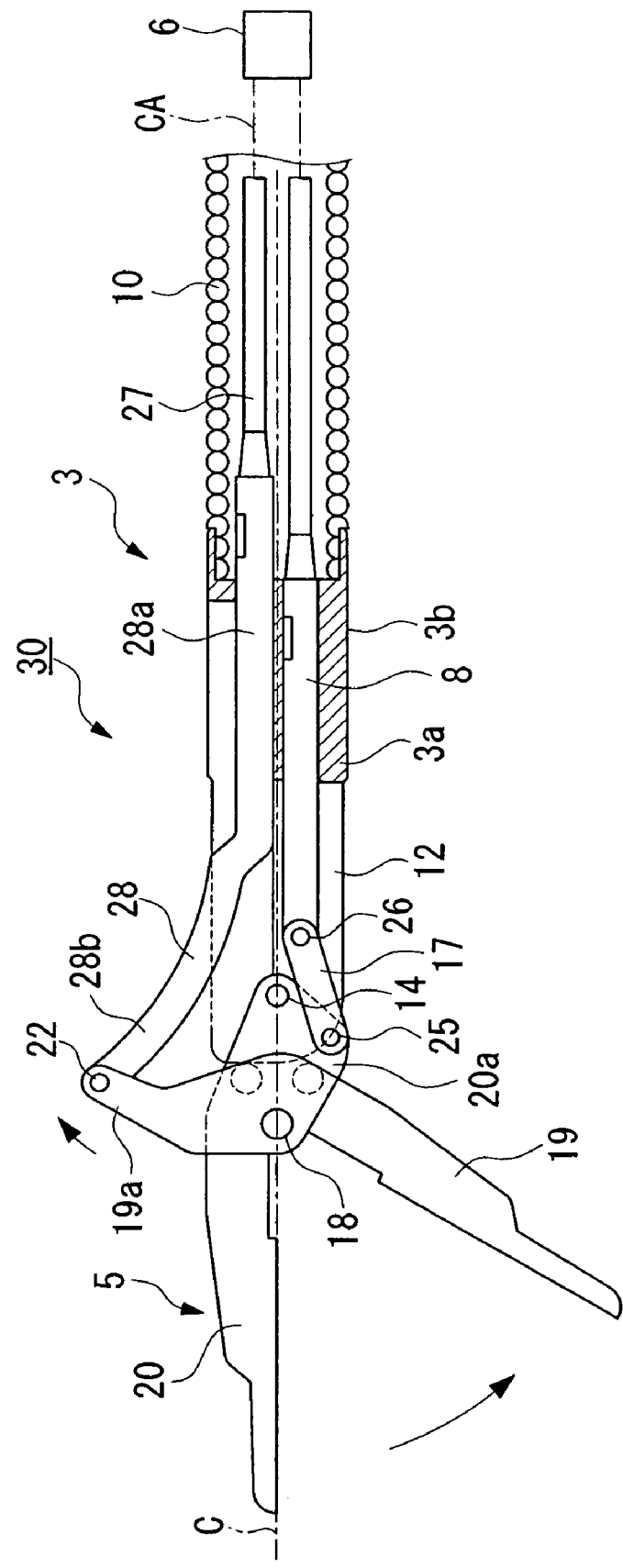
FIG. 7 is a side view of primary parts of the multi-free forceps according to the other embodiment of this invention in an open state, with one portion thereof cut away.
Figure 8:
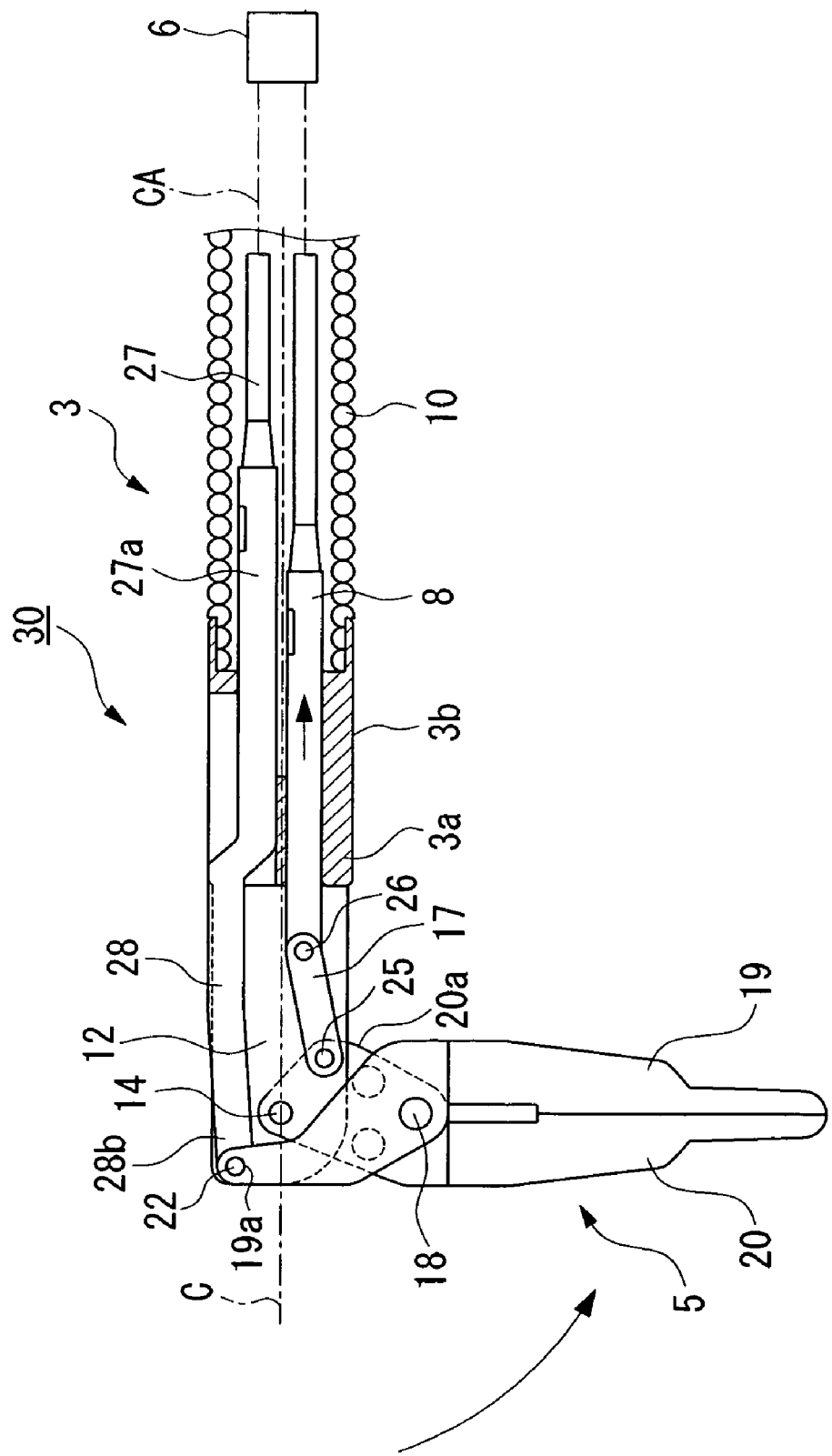
FIG. 8 is a side view of primary parts of the multi-free forceps according to the other embodiment of this invention in an oscillated state, with one portion thereof cut away.
Figure 9:
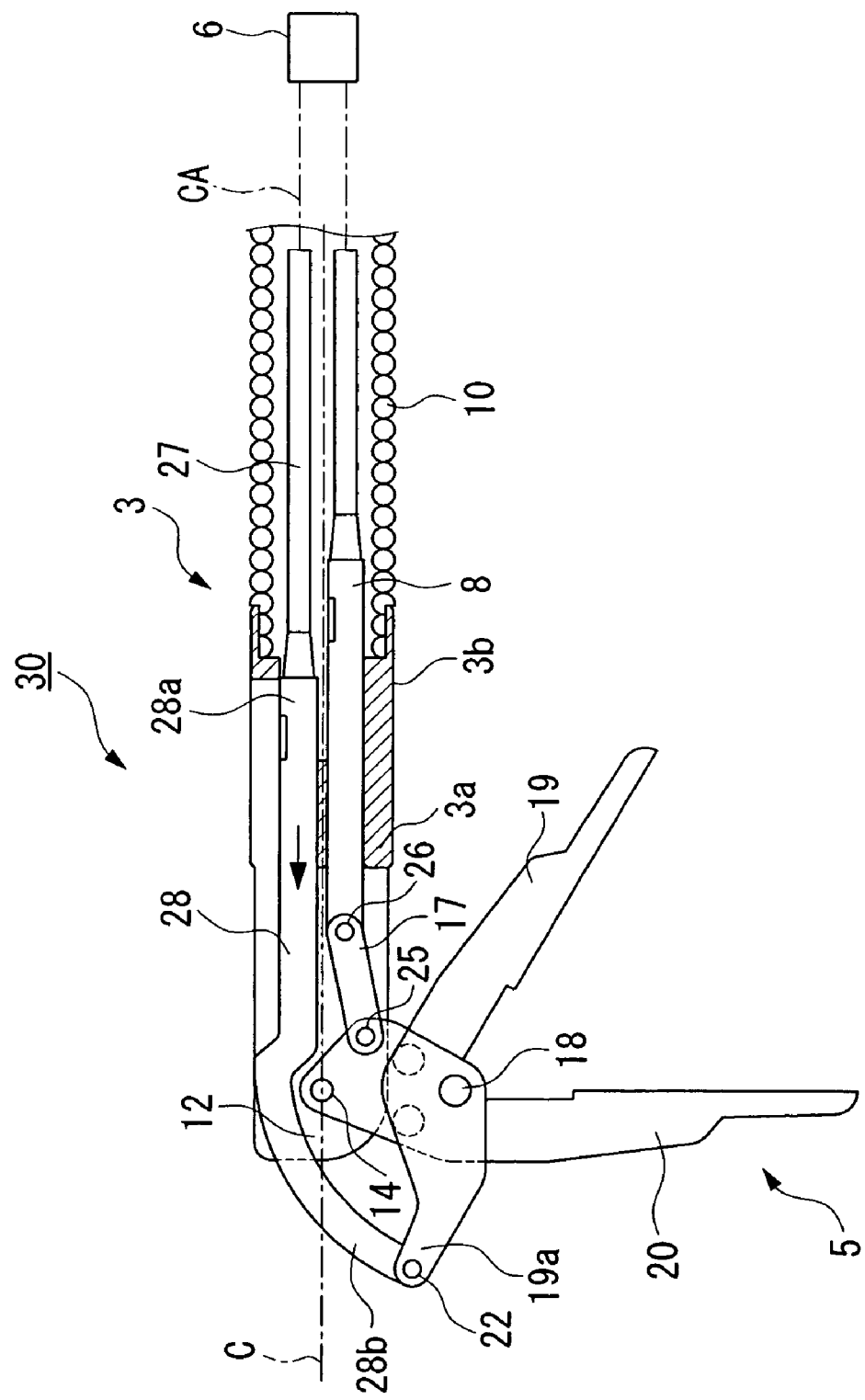
FIG. 9 is a side view of opened primary parts of the multi-free forceps according to the other embodiment of this invention in the oscillated state, with one portion thereof cut away.

Subsequently, as shown in FIG. 5, it will be explained how to further open the first forceps member 19 and the second forceps member 20 from a state where their tips have already been oscillated as shown in FIG. 4.

In the same way as already described, the first control axis member 7 is first moved forward to the tip 3a side by manipulating the control section 6. When the deviating link member 15 moves forward with the first control axis member 7 to the surgical section 5 side along the central axis C, this forward force is transmitted as rotational movement via the fourth pivotal supporting member 23 to the first link member 16, so that the first link member 16 rotates around the fourth pivotal supporting member 23 while moving the third pivotal supporting member 22 forward. As a result, the tip side of the first forceps member 19 moves away from the second forceps member 20 with the second pivotal supporting member 18 as its base point.

In this way, the first forceps member 19 and the second forceps member 20 can be opened with the second pivotal supporting member 18 as their base point.

The tip 15b of the deviating link member 15 moves until it protrudes beyond the tips of the cover members 11 and 12 within the range of the outer peripheral face 3b.

According to this multi-free forceps 1, on the tip 15b side of the deviating link member 15, the region enclosed by the deviating link member 15 and the second control axis member 8 is larger than the region enclosed by the first control axis member 7 and the second control axis member 8. For this reason, even when the first control axis member 7 and the second control axis member 8 are arranged in close vicinity to each other, the deviating link member 15 can be moved further to the tip than the first pivotal supporting member 14. As a result, the surgical section 5 can perform an oscillating operation having a wide angle of rotation. Furthermore, since the tip 15b of the deviating link member 15 does not interfere with the seize member 10, it can be designed without worrying about the thickness of the seize member 10. Therefore, the outer diameter of the tip 15b can be formed in a shape that does not interfere with the first pivotal supporting member 14 without being larger than the outer diameter of the seize member 10.

The present invention is not limited to the embodiment described above, and can be modified in various ways without deviating from its main points.

For example, as shown in FIGS. 6 to 9, a flexible deviating link member 28 comprising a plate-spring, or wire, or the like, may be formed in a single piece with the deviating link member 15 and the first link member 16, and connected at the tip of a first control axis member 27. In this case, the base 28a of the deviating link member 28 is connected to the first control axis member 27, and the tip 28b of the deviating link member 28 and the first forceps member 19 are directly connected with the third pivotal supporting member 22 therebetween.

The multi-free forceps 30 fitted with the deviating link member 28 performs the same functions as the deviating link member 15 and the first link member 16, due to the bending of the deviating link member 28 that is caused by the backward operation of the first control axis member 27.

Furthermore, in a link device for surgical tool in which a hole is provided at the position of the rotational axis, or in a surgical tool fitted with such a link device, the deviating link member 15 or 28 can be used to avoid the hole, enabling the diameter of the control axis members to be made narrow.

The invention described above has the following advantageous effects.

According to the link device of this invention, the outer diameter of the insertion section can be reduced, and the narrow diameter of the control axis members allows the device to be made more flexible.

Further, according to the surgical tool of this invention, since the control axis members do not interfere with the oscillating pivotal supporting members at the time of opening, closing, and oscillating the forceps, the outer diameter of the control axis members can be reduced and made narrower, making it possible to insert the insertion section into an even smaller endoscope forceps or a bodily cavity.

According to this link device for surgical tool, the tip side of the deviating link member is formed on an axial line that extends in parallel with the control axis member at a position deviated toward the outside from the central axis of the control axis member; therefore, even when the surgical section that is connected to the tip of the deviating link member, or another link member, has a section arranged on the axial line of the control axis member, the control axis member can be moved forward and backward without interfering with this section. As a result, the control axis member can be provided near the central axis of the insertion section, and the outer diameter of the insertion section can be made narrower than in conventional devices.

The surgical tool comprises the link device for surgical tool of this invention, and the tip side of the deviating link member is provided further to the outside of the diameter direction of the insertion section than the first rotational axis; therefore, the deviating link member can be moved beyond the first rotational axis position to the tip side. As a result, the surgical section can be made to perform an oscillating operation having a wide angle of rotation.

Since this surgical tool has the constitution described above, the forward and backward movement of the first control axis member rotates the first forceps member around the second rotational axis via the deviating link member, and enables it to be opened and closed with the second forceps member. Further, when rotating the second forceps member around the first rotational axis by the forward and backward movement of the second control axis member, since the first forceps member is connected to the second forceps member via the second rotational axis, the first forceps member can rotate in correspondence with the second forceps member, enabling both to be oscillated.

What is claimed is:

1. A surgical tool comprising:
a pipe-like insertion section having a first control axis member extending in one direction and a second control axis member in line with the first control axis member therein, the first and second control axis members being capable of moving forward and backward;
a surgical section being capable of performing an oscillating operation via the first rotational axis as a centre of a rotation, which is connected via the control axis members and at least one link member, the surgical section being controlled by the forward and backward movement of the control axis members, wherein
when using one of the link members that is directly connected to a tip of the first control axis member as a deviating link member, a tip of the deviating link member is connected to the surgical section directly or via another link member; and
the deviating link member is formed extending in parallel with the first control axis member at a position deviated to the outside from the central axis of the control axis member;
the surgical section comprising a first forceps member and a second forceps member, which are rotatably connected to a second rotational axis at a base side;

the second rotational axis being arranged closer to the tip side of the first forceps member than the first rotational axis;

the deviating link member being connected to a base of the first forceps member directly or via the link member, the first forceps member being capable of being rotated around the second rotational axis by the forward and backward movement of the first control axis member; and the second control axis member being connected to the base of the second forceps member directly or via the link member, the second forceps member being capable of being rotated around the first rotational axis by the forward and backward movement of the second control axis member.

2. A surgical tool as described in claim 1, wherein a tip of the deviating link member is provided further to the outside of the diameter direction of the insertion section than the first rotational axis.

3. A surgical tool as described in claim 1, wherein the link members and the deviating link member are rotatably connected with a plurality of pivotal supporting members.

* * * * *